US007916900B2

(12) United States Patent
Lanier

(10) Patent No.: US 7,916,900 B2
(45) Date of Patent: Mar. 29, 2011

(54) IDENTITY KIT

(76) Inventor: Joan E. Lanier, Farmington Hills, MI (US)

( * ) Notice: Subject to any disclaimer, the term of this patent is extended or adjusted under 35 U.S.C. 154(b) by 1052 days.

(21) Appl. No.: 11/365,369

(22) Filed: Mar. 1, 2006

(65) Prior Publication Data

US 2006/0196785 A1    Sep. 7, 2006

Related U.S. Application Data

(60) Provisional application No. 60/657,471, filed on Mar. 1, 2005.

(51) Int. Cl.
*G06K 9/00*    (2006.01)
(52) U.S. Cl. ......... 382/115; 206/223; 206/570; 382/128
(58) Field of Classification Search .................... 340/5.6, 340/5.83, 573.1; 382/115, 124; 713/182; 206/223, 569, 570
See application file for complete search history.

(56) References Cited

U.S. PATENT DOCUMENTS

| | | | | |
|---|---|---|---|---|
| 4,763,791 | A * | 8/1988 | Halverson et al. | 206/570 |
| 5,101,970 | A | 4/1992 | Turner | 206/223 |
| 5,728,341 | A * | 3/1998 | Kim, II | 264/222 |
| 5,856,102 | A | 1/1999 | Bierke-Nelson et al. | 435/6 |
| 5,863,202 | A * | 1/1999 | Fontenot et al. | 433/215 |
| 5,876,926 | A * | 3/1999 | Beecham | 435/5 |
| 5,978,493 | A * | 11/1999 | Kravitz et al. | 382/115 |
| 6,779,665 | B2 * | 8/2004 | Bolanos | 206/569 |
| 7,308,123 | B2 * | 12/2007 | Fenrich et al. | 382/125 |
| 7,405,666 | B2 * | 7/2008 | Lane et al. | 340/573.1 |
| 2003/0113906 | A1 * | 6/2003 | Sangha et al. | 435/287.2 |
| 2003/0197853 | A1 * | 10/2003 | Fenrich | 356/71 |
| 2004/0049956 | A1 * | 3/2004 | Li | 40/124.06 |
| 2004/0109608 | A1 * | 6/2004 | Love et al. | 382/224 |
| 2004/0116826 | A1 * | 6/2004 | Jung et al. | 600/562 |
| 2006/0085226 | A1 * | 4/2006 | Kamber | 705/2 |
| 2007/0183633 | A1 * | 8/2007 | Hoffmann | 382/116 |

OTHER PUBLICATIONS

Hines, Matt, "MedicAlert to Arm Patients with USB Drive," CNET News.com, Jan. 5, 2005, (http://news.com.com/MedicAlert+to+arm+patients+with+USB+drives/2100-7353 3-5513).
"CupMed Introduces Personal HealthKey Secure, Private, Portable Medical Records Enabled by Flush-Based Technology From M-Systems' DiskOnKey," Press Release, CupMed, Jun. 10, 2003 (http://www.cupmed.com/news/press\press_release_vlrt_20.asp).

* cited by examiner

*Primary Examiner* — Gregory M Desire
(74) *Attorney, Agent, or Firm* — Gifford, Krass, Sprinkle, Anderson & Citkowski, P.C.

(57) ABSTRACT

An improved method of collecting identifying information (such as samples and data) from a subject to facilitate later identification of said subject. Identifying information may include biological samples, medical records, photographs and videos, audio recordings, odor characterization (of body or exhalations, for example, characterizing a disease such as diabetes), fingerprints, dental records, and the like. Such a identification kit may be comprised of some combination of the following items: a data recording medium (such as a CD, DVD, flash card, or other memory card, other memory device, or printable data such as a barcode or chart); a first receptacle (such as a plastic bag, vial, or other container) for hair samples; a dentition recorder such as a tooth impression wafer; a second receptacle for a blood sample, which may be part of a blood typing kit or other blood sample collection kit; address information, such as a mailing label which may be supplied already attached to an envelope or other mailing container, or e-mail address, or URL, for sending a copy of collected identifying information to an administrating business; a cheek retractor to facilitate obtaining a dentition record; and a fingerprint kit.

15 Claims, 15 Drawing Sheets

ID INTERNATIONAL     FORMAT     IT'S REALLY ME & ONLY ME ID
PART I & PART IV - TO BE PERFORMED BY DENTAL OFFICE
TAKE X-RAYS,TOOTHPRINTS/DNA SAMPLES,PHOTOS OF FACE,HANDS AND FINGER PRINTS

---

PART II      SCRIPT      TODAY'S DATE_____
FULL NAME _____ NICKNAME_____

AGE _____ BIRTHDATE _____ mm _____ dd _____ yr. PLACE OF BIRTH_____

HEIGHT _____ WEIGHT _____ SEX M/F   SCHOOL,CURRENT OR PAST EMPLOYER_____
'ZOOM) EYE COLOR _____ HAIR COLOR _____ NATIONALITY_____

LIST ANY LANGUAGE YOU SPEAK,READ,WRITE OR UNDERSTAND _____

DO YOU HAVE A BIRTHMARK,DIMPLE,SCAR,MOLE,TATOO,BROKEN BONE,PROSTHETIC PART IE. HEARING AID,
LIMB,JEWLERY ALWAYS WORN, BODY PIERCING OR OTHER IDENTIFYING MARKS? WHERE ARE
THEY?_____
LIST ANY HOBBIES _____

PART III Privacy Items SSN #_____ PASSPORT #_____

ADDRESS_____ CITY_____ STATE_____ ZIP_____

PHONE (#)S (H)_____ (W)_____ (CELL)_____ E-MAIL_____

MOTHER'S FULL NAME (LIVING/DECEASED)_____

PHONE HOME _____ WORK_____ CELL_____

FATHER'S FULL NAME (LIVING/DECEASED)_____

PHONE HOME _____ WORK_____ CELL_____

LIST ALL SIBLINGS, SPOUSES & CHILDREN ( MARK * IF DECEASED AND FROM WHAT ) (USE BACK)

CLOSE RELATIVE OR FRIEND'S NAME_____ PHONE#_____
MEDICAL ALERT: BLOOD TYPE_____ CIRCLE IF WEARING : GLASSES, CONTACTS OR BRACES

A) ASTHMATIC_____ B)DIABETIC_____ C)ALLERGIES_____

D) HIGH BLOOD PRESSURE _____ E) HEART CONDITION_____ SBE NEEDED YES/NO

F) MEDICATIONS CURRENTLY TAKING _____

G) OTHER _____ H)RIGHT OR LEFT HANDED_____
RECOMMENDED FOLLOW UP AT AGES 8,12 ,16 OR BEFORE COMPLETING HIGH SCHOOL THEN PER 3-5 YEARS.

SIGNATURE OF PATIENT OR PARENT/GUARDIAN OF MINOR _____

---

PART IV   X-RAYS (LIST#) FBW____ PA'S____ RCT'S ON_____ LESIONS_____
TOOTH PRINTS OR OTHER DNA SAMPLE TAKEN: (TYPE) IE. BLOOD, HAIR OR _____
ORAL SCREEN FINDINGS: MISSING TEETH: ALL OR #'S _____
1)BRIDGE WORK: UR UL LR LL   PARTIAL U/L   IMPLANTS ON #S_____
2)RESTORTIONS ON #S_____ CROWNS ON #S_____
3)CARRIES SEEN ON: NONE OR TOOTH # ' S_____
4)ORAL HYGIENE / PERIO CONDITION    GOOD    FAIR    POOR
5)CROWDING OF TEETH (POSSIBLE NEED FOR BRACES) YES/NO   BRACES WORN IN THE PAST ? YES/NO
6)EXTRACTION NEEDED WITH TOOTH #'S_____
7)TORI- MAX / MAND   8) OTHER FINDINGS_____
TAKE PHOTOS OF SCRIPT, IMMUNIZATION FORM, BIRTH CERTIFICATE, X-RAYS ,TOOTHPRINTS , HAIR ,FINGER
PRINTS OR OTHER SAMPLES AND INSURANCE INFORMATION i.e. FAXED BENEFITS .

FIGURE 1

HYPER SEARCH BODY IDENTIFIERS

| BODY PART | | IDENTIFIER/CHARACTER |
|---|---|---|
| A. HEAD/FACE | R/L | 1. MOLE |
| B. EARS | R/L | 2. BIRTHMARK |
| C. EYE BROW | R/L | 3. SCAR |
| D. EYE | R/L | 4. DIMPLE |
| E. NOSE | R/L | 5. TATOO |
| F. MOUTH | R/L | 6. TORUS |
| G. LIPS | U/L | 7. PROSTHESIS |
| H. TONGUE | R/L | 8. BODY PIERCING |
| I. CHIN | | 9. BROKEN BONE |
| J. NECK | R/L | 10. MISSING APPENDAGE |
| K. CHEST | R/L | 11. JEWELRY ALWAYS WORN |
| L. ARM | R/L | 12. BEARD |
| M. HAND | R/L | 13. MUSTACH |
| N. ABDOMEN | R/L | 14. HEARING AID |
| O. BACK | R/L | 15. DENTURE |
| P. BELLY BUTTON | | 16. PARTIAL DENTURE |
| Q. PELVIC AREA | R/L | 17. CROWN |
| R. BUTTOCK | R/L | 18. BRIDGE |
| S. THIGH | R/L | 19. IMPLANT |
| T. KNEE | R/L | 20. ROOT CANAL |
| U. LEG | R/L | 21. GLASSES |
| V. FOOT | R/L | 22. CONTACT LENSES |
| | | 23. FRECKLES |

Samples

5/R/K     is a tatoo on right chest     2/R/L     is a birthmark on right arm

4/R+L/A     are dimples on face     11/R+L/M+J+B+L     is jewelry always worn on 4/I     is a dimple on chin                                                  right and left hands, necklace, 8/P     is a pierced belly button                                 earrings and bracelets 3/L/S     is a scar on left thigh

FIGURE 2

It's Really Me & Only Me ID

KIT INSTRUCTIONS: Take all items below to your dentist for an exam and processing.

---

CONTENTS:

2 DVDs in jewel cases                    2 Cheek retractors ( small and large)

2 Plastic bags for hair samples          2 Fingerprint kits

2 Teeth impression wafers                Toothbrush, floss, disclosing tablets

1 Blood typing kit (caution-do not use if taking anticoagulants or have a bleeding problem)

2 Storage bubble envelopes               Bracelet- It's Really Me & Only Me ID

3 Forms (Format,Insurance Sheet,         1 Instruction Sheet
     Consent Form)

---

Complete All Forms Before Going to your Dentist
USE BLUE INK- this is necessary to identify original forms A, B, and C

(A) FORMAT          (B)INSURANCE SHEET FOR          (C)CONSENT FORM
                    1 OR 2 CARRIERS
PART II             IF QUESTIONS CHECK WITH
PART III            YOUR BENEFITS OFFICE

ALL LINES OF PARTS II AND III OF FORMAT SHOULD BE ANSWERED!!!
LEAVE NO BLANK SPACES. IF YOU DO NOT HAVE AN ANSWER PLEASE PUT --
OR WRITE NONE IN THE SPACE

---

Bring old Explanation of Benefits or other insurance vouchers. This will help to verify the accuracy of your insurance benefits. (The dentist will get a fax of your insurance information once you arrive at the office. This will tell us your benefits and how much money you have remaining available for treatment.)

FOR FILMING PURPOSES TO BE INCLUDED ON DVD OR FLASH DRIVE PLEASE BRING THE FOLLOWING:

1. Immunization forms for each child      5. Passport
2. Birth certificate                      6. State ID card
3. Medical and Dental Insurance cards     7. Driver's License
4. Work visa if applicable

*For accuracy weigh yourself at home with minimal clothing.
***If you do not have a dentist or your dentist does not participate in this program call (248)948-1998 or fax (248)948-0007 for referral to a participating office.

ID INTERNATIONAL  FORMAT  IT'S REALLY ME & ONLY ME ID
PART I & PART IV - TO BE PERFORMED BY DENTAL OFFICE
TAKE X-RAYS, TOOTHPRINTS/DNA SAMPLES, PHOTOS OF FACE, HANDS AND FINGER PRINTS

---

PART II SCRIPT  TODAY'S DATE_____ IDI# _____

FULL NAME _____ NICKNAME _____

AGE _____ BIRTHDATE _____ mm ____ dd _____ yr. PLACE OF BIRTH _____

HEIGHT ____ WEIGHT ____ SEX M / F  SCHOOL,CURRENT OR PAST EMPLOYER _____
(ZOOM) EYE COLOR _____ HAIR COLOR _____ NATIONALITY _____

LIST ANY LANGUAGE YOU SPEAK, READ AND WRITE OR UNDERSTAND _____
DO YOU HAVE A BIRTHMARK, DIMPLE, SCAR, MOLE, TATOO ,BROKEN BONE,PROSTHETIC PART IE. HEARING AID,
LIMB, JEWLERY ALWAYS WORN, BODY PIERCING OR OTHER IDENTIFYING MARKS? WHERE ARE
THEY ?_____

LIST ANY HOBBIES _____
PART III Privacy Items SSN #_____ PASSPORT #_____

ADDRESS_____ CITY_____ STATE_____ ZIP_____

PHONE (#) S (H)_____ (W)_____ (CELL)_____ E-MAIL_____

MOTHER'S FULL NAME (LIVING/DECEASED)_____

PHONE HOME _____ WORK_____ CELL_____

FATHER'S FULL NAME (LIVING/DECEASED)_____

PHONE HOME _____ WORK_____ CELL_____

LIST ALL SIBLINGS, SPOUSES & CHILDREN (MARK * IF DECEASED AND FROM WHAT) (USE BACK)

CLOSE RELATIVE OR FRIEND'S NAME_____ PHONE#_____
  MEDICAL ALERT: BLOOD TYPE_____ CIRCLE IF WEARING: GLASSES, CONTACTS AND/ OR BRACES

A) ASTHMATIC_____ B) DIABETIC_____ C) ALLERGIES_____

D) HIGH BLOOD PRESSURE_____ E) HEART CONDITION_____ SBE NEEDED YES/NO

F) MEDICATIONS CURRENTLY TAKING _____

G) RIGHT OR LEFT HANDED _____ H) OTHER_____
RECOMMENDED FOLLOWS UP AT AGES 8, 12, 16 OR BEFORE COMPLETING HIGH SCHOOL, THEN EVERY 3-5 YEARS.

SIGNATURE OF PATIENT OR PARENT/GUARDIAN OF MINOR _____

---

PART IV  X-RAYS (LIST# S )  PBW_____ PA'S_____ RCT'S ON_____ LESIONS_____
TOOTH PRINTS OR OTHER DNA SAMPLE TAKEN: (TYPE) IE. BLOOD, HAIR OR _____
ORAL SCREEN FINDINGS: MISSING TEETH: ALL OR #'S _____
1) BRIDGE WORK: UR UL LR LL  PARTIAL U/L  IMPLANTS ON #S_____
2) RESTORTIONS ON #S_____ CROWNS ON #S_____
3) CARRIES SEEN ON: NONE OR TOOTH # 'S_____
4) ORAL HYGIENE / PERIO CONDITION    GOOD    FAIR    POOR
5) CROWDING OF TEETH (POSSIBLE NEED FOR BRACES) YES/NO BRACES WORN IN THE PAST? YES/NO
6) EXTRACTION NEEDED WITH TOOTH #'S_____
7) TORI- MAX / MAND  8) OTHER FINDINGS_____
TAKE PHOTOS OF SCRIPT, IMMUNIZATION FORM, BIRTH CERTIFICATE, X-RAYS, TOOTHPRINTS, HAIR, FINGER
PRINTS OR OTHER SAMPLES AND INSURANCE INFORMATION i.e. FAXED BENEFITS.

DENTIST'S SIGNATURE_____ PRINT NAME_____ DATE_____

| DENTAL INSURANCE COMPANY #1 | DENTAL INSURANCE COMPANY#2 |
|---|---|
| Name of Ins. Co._____ | Name of Ins. Co._____ |
| Address:_____ | Address:_____ |
| _____ | _____ |
| Phone#_____ | Phone#_____ |
| Group#_____ EFC:_____ | Group#_____ EFC:_____ |
| This Dental Insurance is Provided for: | This Dental Insurance is Provided for: |
| Name of Patient: _____ DOB____ | Name of Patient:_____DOB____ |
| Subscriber's Name:_____ | Subscriber's Name:_____ |
| Subscriber's Social Security #:_____ | Subscriber's Social Security#:_____ |
| Subscriber's Date of Birth:_____ | Subscriber's Date of Birth:_____ |
| Subscriber's Employer:_____ | Subscriber'sEmployer:_____ |

FIGURE 3C

Consent for Photography or Videotaping
(for the Media or Educational Purposes)

_____
Child's or Patient's Name (Print)

Date of Birth_____ Age_____ SS#_____

I hereby give consent to have photographs, videotaped images, or other images made of myself or my family member and/ or consent to interviews with a member of the news Media or a representative of Joan E. Lanier D.D.S., M.S.
All records are property of the dentist but I will be given a copy of these images. I understand that these images will be protected with HIPPA compliance. I also give consent for a dental screening exam during this procedure.

_____
Patient's or Authorized Representative's printed name

_____
Patient's or Authorized Representative's signature

_____
Relationship to patient if other than self ie. Mother, Father or Guardian

_____
Witness

_____
Witness's signature

_____
Date

FIGURE 3D toothprints®

Fabrication Technique

- Remove contents of Toothprints package and place on tray or counter.
- Write patient's name and date of impression in ink on bag provided.
- Immerse Toothprints wafer into hot water, 170°F (77°C) or greater, for a minimum of 15 to 30 seconds to soften.
- Instruct patient to open mouth as wide as possible for insertion.
- Place softened Toothprints wafer into patient's mouth on lower arch. (Wafer can be stretched to fit any arch form).
- Instruct patient to bite hard onto softened wafer and hold for 20 seconds to record dentition and capture saliva.
- Remove Toothprints wafer from patient's mouth and place in bag on counter to cool down for 2 to 3 minutes. (Do not rinse Toothprints impression after mouth removal or you will risk losing captured DNA in saliva.)
- Give finished, packaged Toothprints to parent/guardian for storage.

Kerr Corporation  1717 West Collins Avenue, Orange, CA 92867

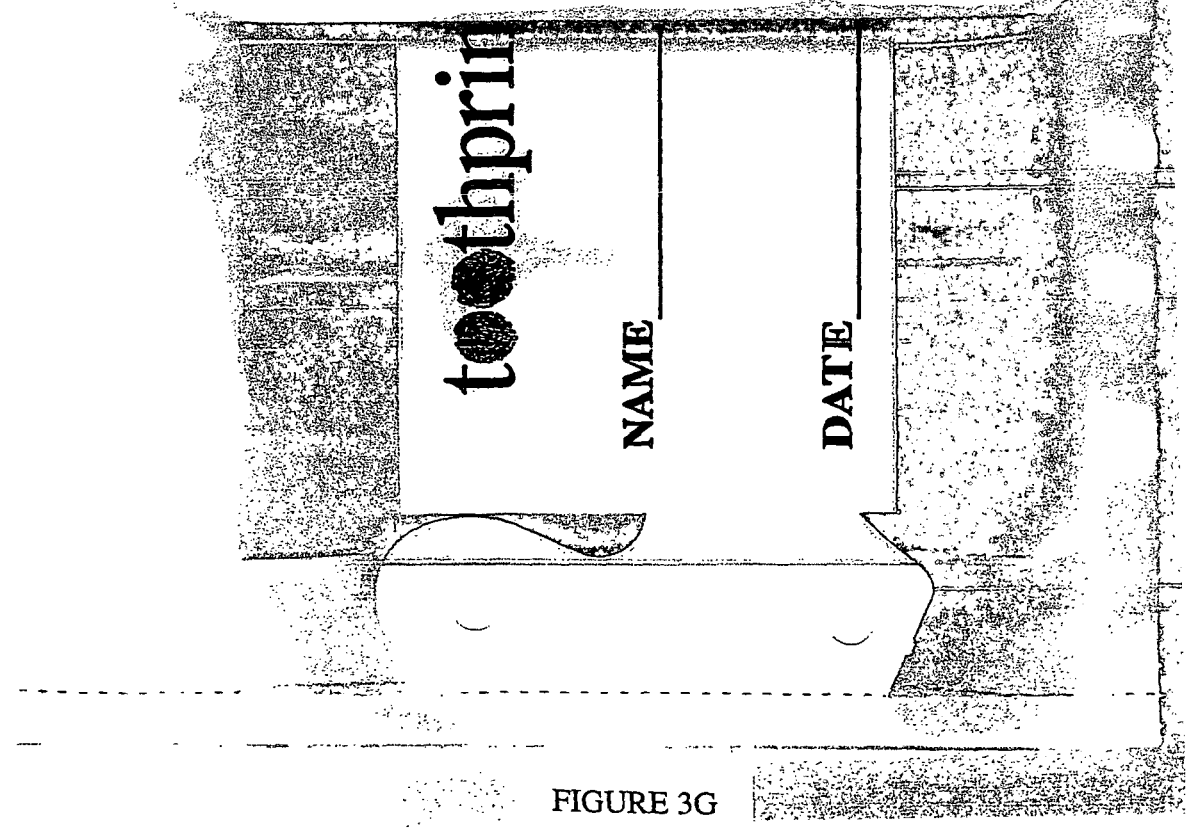

FIGURE 3G

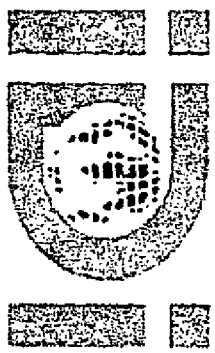
FIGURE 3I

FIGURE 3J

IDENTITY KIT

REFERENCE TO RELATED APPLICATION

This application claims the benefit of U.S. Provisional Patent Application Ser. No. 60/657,471, filed Mar. 1, 2005, the entire content of which is incorporated herein by reference.

FIELD OF THE INVENTION

The present invention relates to methods and apparatus for characterizing a living subject, in particular to a kit for collecting information to facilitate later identification of a subject.

BACKGROUND OF THE INVENTION

A child is reported missing every 40 seconds in the United States according to the National Center for Missing and Exploited Children. 1 in every 42 children will become missing, abducted, lost or runaway. Each day 2000 children are reported missing and 725,000 go missing in a year. There are now 4.5 million people having Alzheimer's disease now, with numbers increasing to 11 to 15 million by 2020. Approximately 60% of Alzheimer's patients will wander at some point, and need to be returned to a guardian.

Hence, improved methods and apparatus allowing reliable identification of a subject are urgently needed. Collection of DNA samples can be helpful, but this does not allow rapid identification of a subject without sophisticated equipment.

U.S. Pat. No. 5,101,970 to Turner describes a personal identification system, but fails to disclose the collection of dental records or video information.

U.S. Pat. No. 5,856,102 to Bierke-Nelson et al. describes home storage of DNA samples, but also fails to describe dental characterization or video information.

BRIEF DESCRIPTION OF THE DRAWINGS

FIG. 1 illustrates a script to assist collection of identifying information;

FIG. 2 illustrates a hyper-search data identification system; and

FIGS. 3A-3M illustrate the contents of an example kit.

DETAILED DESCRIPTION OF THE INVENTION

Figure 3E:
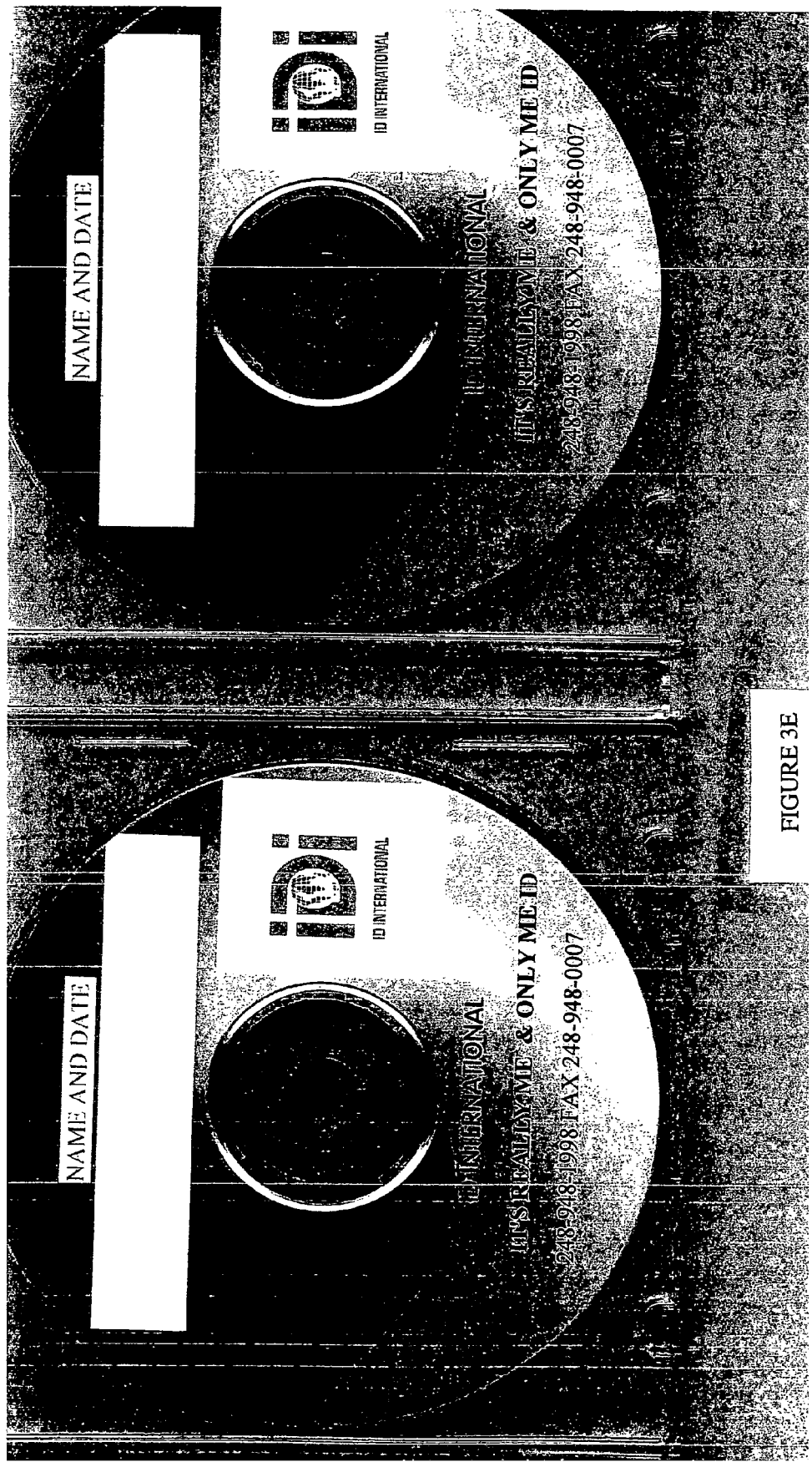

In this specification, the term "subject" refers to the subject, such as a child, elderly person, or other person, from which identifying information is collected. Identifying information may include biological samples, medical records, photographs and videos, audio recordings, odor characterization (of body or exhalations, for example, characterizing a disease such as diabetes), fingerprints, and the like.

Dental records are particularly useful. Dentition generally changes slowly with time, and is resilient to adverse conditions. Hence, collection of dental information is very helpful to future identification of a subject.

Collection of Identifying Information

An improved method of collecting identifying information (such as samples and data) from a subject to facilitate future identification comprises: collecting one or more biological samples, collecting a dental impression or otherwise obtaining a record of dentition, and recording images, such as a video, of the subject.

Biological samples collected may include a blood sample, hair sample (such as follicles), cheek swab or other collected cells for use with DNA identification (such as from the inner cheek including the inner lips), urine sample, and the like.

Recording images, such as a video, of the subject may include recording images of one or more facial expressions, identifying marks (such as tattoos, skin blemishes, scars, birthmarks, and the like), jewelry (including body piercing or other distinct body ornamentation), and recording images of the inside of the subject's mouth.

The images includes a plurality of images, and may include a real-time video recording of the subject in a largely sedentary position (such as sitting in a chair), a sequence of still images, recordings of subject physical activity, or some combination thereof. The video recording may further include an audio track, for example used to record the subject's voice. A separate audio recording may be provided. Still images may be separate files, such as digital photographs, or included in a video file.

The images may show the subject in various activities, such as walking (to show gait, limp, or child's walk), running, engaged in emotional outbursts, acting in a characteristic manner (for example, behavior, mannerisms, speech patterns, or other behavior characteristic of a disease, emotional problem, psychiatric problem, or other involuntary behavioral characteristic such as tremors). The images may include a video interview, allowing voice recognition and more reliable visual identification. Images can be recorded of dentition, eyes, retinal details, hands, and facial profiles, and the subject's body from various angles such as front, side, back, and various oblique angles.

The method may further include recording one or more physical identifiers of the subject, such as fingerprints, foot or toe prints, dental chart, dental x-ray, retinal scan, medical x-ray (for example, showing identifying characteristics such as an implanted metal plates), ultrasound image, gum print if no teeth are available (for example, for the elderly or newborns), or other characterization information (such as written description, chart, form, photographs, etc.) of identifying features.

Collected dental characteristics can include one or more of the following: a tooth imprint, dental chart, dental image such as a photograph, laser scanning of tooth profiles, fluorescent imaging, ultrasound imaging, colorimetry (shade determination), chemical analysis of enamel, and a dental x-ray. Numerical data can be extracted from collected characteristics, such as tooth dimensions, relative tooth positioning, and gum interface locations. A dental chart can be filled out, identifying the location of previous dental work such as fillings.

The method may also include collecting other physiological, demographic, medical, or family information, such as height, weight, appearance, ethnicity, relative identity, medical history, medical history of relatives, occupation, occupational history, contact information, alternative contact information, emergency contact information, insurer information, numbers from any identifying documents such as passports and drivers licenses, and the like.

FIG. 1 shows a script (questionnaire) for collecting identifying information.

FIG. 2 illustrates a hyper search identification system. A form is used to accept a first code relating to an identifying feature, and an optional second code (or modifier for the first code) relating to location or other aspect of the identifying feature. Other codes may also be used, for example to describe other aspects of the feature, such as size, condition, location, visibility, medical diagnosis, and the like. For example, if the subject has a large, hairy mole on the nose, a first code may indicate a mole, and second, third, and fourth codes (or modifiers to the first code) used to indicate the large size, condition (hairiness), and location of the feature indicated by the first code. The system can use a form, such as shown in FIG. 2, or use a computer program to prompt and accept code entry. The codes assist later identification of the subject. For example, if a suspected subject is to be identified, a code can be quickly generated from the appearance of the subject, and used to narrow down the possible subject matches. Other identifying information can then be used to confirm the identity of the subject.

The method may further include recording copies of insurance forms, identity documents (such as a driver's license, passport, other identity card), and other documents associated with the subject. These copies may form part of the video, for example as video stills, or may be recorded as separate electronic or physical copies.

The collected identifying information can be digitized, for example by scanning or otherwise imaging forms, and a plurality of copies of the information made. One copy can be provided to the subject or caregiver, and a second copy supplied to a central database.

Kit for Collecting Information

An improved kit to facilitate collection of identifying information for a subject comprises some combination of the following items (and may also include two or more of any given item): a data recording medium (such as a CD, DVD, flash card, or other memory card, other memory device, or printable data such as a barcode or chart); a first receptacle (such as a plastic bag, vial, or other container) for hair samples; a dentition recorder such as a tooth impression wafer; a second receptacle for a blood sample, which may be part of a blood typing kit or other blood sample collection kit; address information, such as a mailing label which may be supplied already attached to an envelope or other mailing container, or e-mail address, or URL, for sending a copy of collected identifying information to an administrating business; a cheek retractor to facilitate obtaining a dentition record; and a fingerprint kit.

The kit may also include a toothbrush, floss, and disclosing tablets, particularly if the kit is supplied by a dental professional.

The data recording medium may be a medium insertable into an electronic device, or may be an intrinsic component of a device, such as the internal memory of a cell-phone, computer, camera, or other electronic device.

The kit may be supplied to the subject, or a caregiver having a relationship with the subject. The caregiver may be a parent, child, other relative, guardian, medical professional such as a nurse or doctor, dentist, or other person.

In one example, the subject or caregiver purchases the kit, and then the subject visits a dentist or other medical professional with the kit. The medical professional administers the collection of identifying information. For example, a dentist may perform a dental exam, and record the results on a dental chart, which can be part of the kit. A bite impression can be collected. The bite impression can be converted to electronic data, for example as a topographic map of the subject's teeth, and stored on the data storage medium.

The medical professional can also uses video recording equipment, such as a video camera, to record video information. All identifying information can be stored on the data recording device.

In another example, a software program prompts for the collection of identifying information. The information, which can include photos, videos, scanned paper documents, forms filled out on paper or a computer, voice recordings (for voice analysis or for answers to questions) can be stored on the data recording medium. Identifying information can also be stored as a mixture of media, such as printed information and electronic information.

The kit may include a form (such as a questionnaire) for collecting information, such as discussed above in relation to FIG. 1. The kit may also contain a form for generating searchable codes correlated with identification data, such as discussed above in relation to FIG. 2. The kit may also include a consent form for imaging (photography or videotaping), and for storage of images, for example in a database.

In other example, the data storage medium may not be part of the kit. The data storage medium can be a remote server or database, a computer under the control of the medical professional or associated professional (such as an insurer), or other device.

Identifying information can be transmitted to a data storage medium through a network, such as the Internet, by methods including wired and wireless communication. For example, data can be stored on the memory of a portable electronic device, and transmitted by the device to a remote computer.

The kit can be purchased by a subject or a caregiver of the subject. The kit may further include instructions for use, directed to the subject, to the caregiver, and/or to the medical professional.

Methods of Identifying a Subject

In some cases, a situation will arise where the subject needs to be identified. For example, the subject may be: trying to gain entry into a secure area (such as a military base, airport, hospital, government building, and the like); crossing a national boundary, wandering around in public in a dazed and/or confused manner; dead or otherwise non-responsive; military personnel missing in action; claiming one identity with another identity suspected, for example, a suspected escaped prisoner, fraudster, identity thief, or similar; an unaccompanied minor; in a public area wearing clothing suggestive of a medical problem, such as a person walking along a sidewalk in a hospital gown; claiming one age where another is suspected; asking for assistance, such as asking "Who am I?"; victims of an accident, natural disaster, or other injurious event; situations where proof of death is required; or otherwise in a situation where accurate identification would be advantageous.

In such cases, a third party will try to establish a true identity of the subject. The third party may be another person, such as police, fireman, teacher, or medical professional, or a group of persons, or in some cases may be an automated identification system.

In one improved method, the third party contacts a location where identifying information is stored. The location may be a database, web site, person or computer associated with a business which maintains a database of the identifying information, or may correspond to a caregiver or other medical professional, hospital, or other location. The person requesting the information may have to verify their identity using an analogous method.

Verified identifying information for the subject identity is transmitted to the third party, who then compares the information with the person who is possibly the subject. The comparison may also be carried out by an automated system. The third party may request the subject provide information, such as fingerprints, a view of dentition, or other information analogous to that previously collected. Transmission of the identifying information to the third party can be over a network such as the Internet.

In another method, relatives, guardians, caregivers, or other person having a relationship with the subject supply the characteristic information to a third party. The characteristic information is compared with the subject, and subject identity is verified or not verified. The third party may receive the identifying information first, and then attempts to locate the subject. Images of the subject can be used by a surveillance system to detect the subject using computerized image analysis techniques.

Business Model

A business can be established to supply identification kits, such as those described herein, and/or store identifying information collected from a subject. The business may also collect identifying information, and store the identifying information in a database. Authorized parties, such as the police, may access the identifying information through provision of a suitable authorization code. The business may also alert the caregiver if an inquiry is made relating to the subject, and may provide location information for the subject to the caregiver. The dentist or other person collecting the identifying information may transmit (such as fax or e-mail) collected identifying information to a central database maintained by the business. The business may supply the information in the case of law enforcement requests or emergency situations. A customer, such as the caregiver or insurer of the subject, may pay a subscription for the storage and dissemination capability. A charge can be made for storing recorded information for an agreed time period, such as a number of years.

Example Kit

An example kit for collecting identifying information from a subject comprises a container in which the following items are contained: a DVD or other data storage device, a receptacle (such as a plastic bag) for hair samples, a tooth impression wafer, a blood typing kit, a mailing label (which may be on an envelope), a cheek retractor, a fingerprint kit, a toothbrush, floss, and disclosing tablets. Duplicates of some or all items may be provided so that one set may be retained by the subject or a representative of the subject and another retained by a storage provider. A necklace, bracelet, or other identifier can be provided to show the subject has gone through the identification process, which may be similar to or combine the function of a medical alert bracelet or necklace.

The kit may also contain a cotton swab or membrane for collection of DNA, a dental chart to be filled out by a dentist after a dental exam, and other items.

A tooth impression wafer such the TOOTHPRINTS wafer made by Kerr Corp., Orange, Calif. can be used. The wafer records dentition, and also captures DNA samples. A suitable blood typing kit, the ELDONCARD 2511, is available from North American Pharmacal, Inc., of Norwalk, Conn.

Figure 3F:
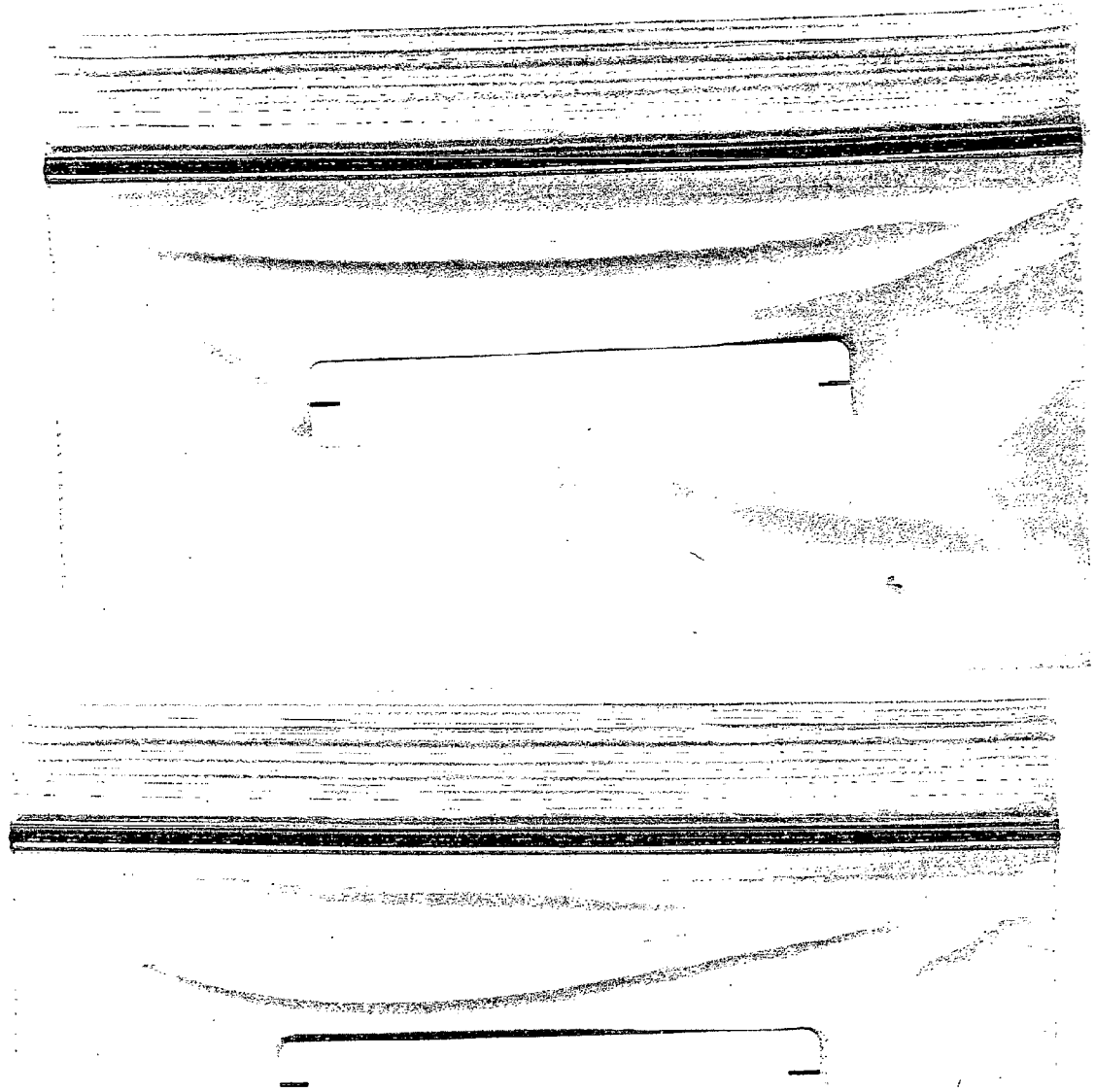
Figure 3H:
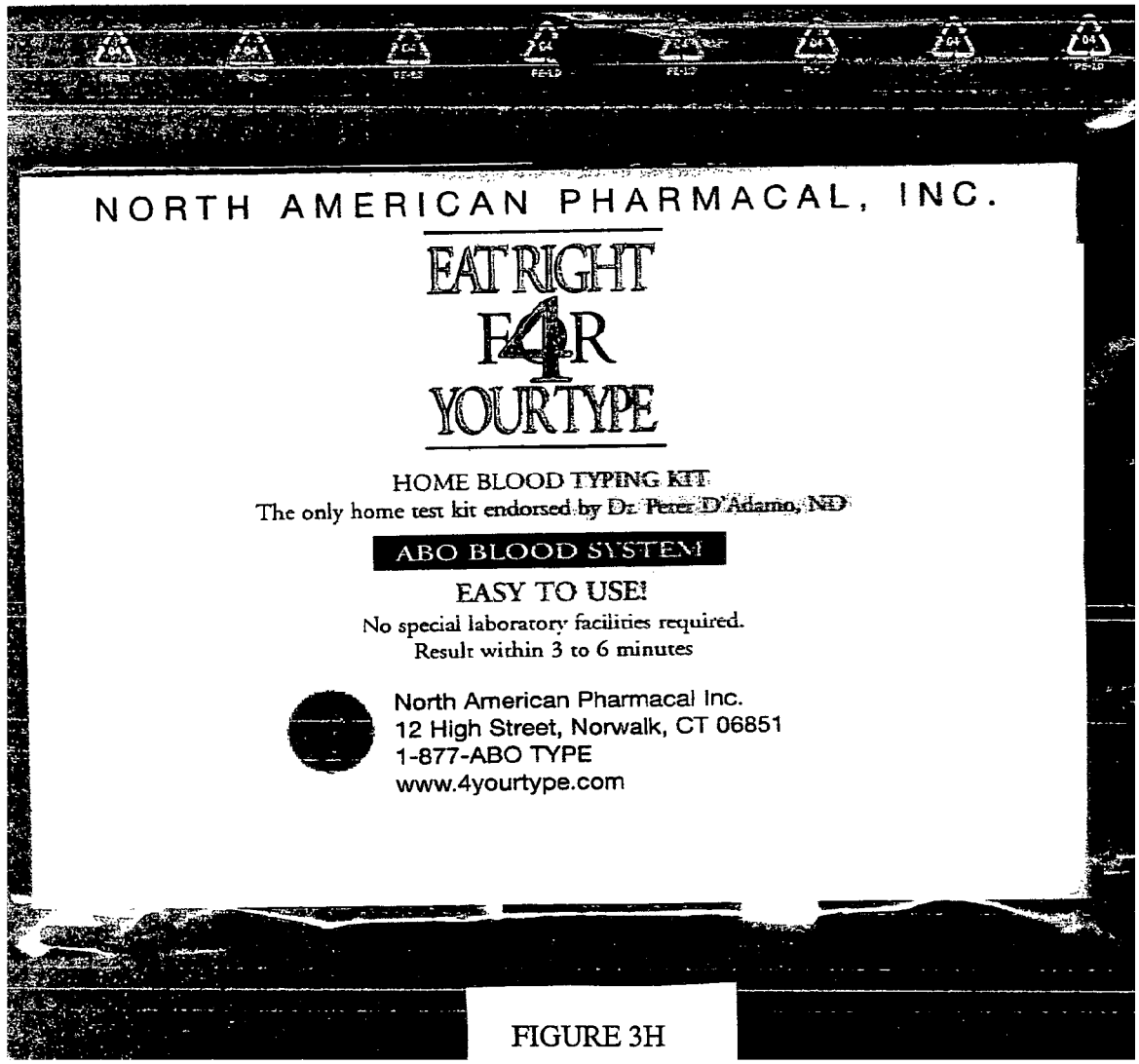
Figure 3K:
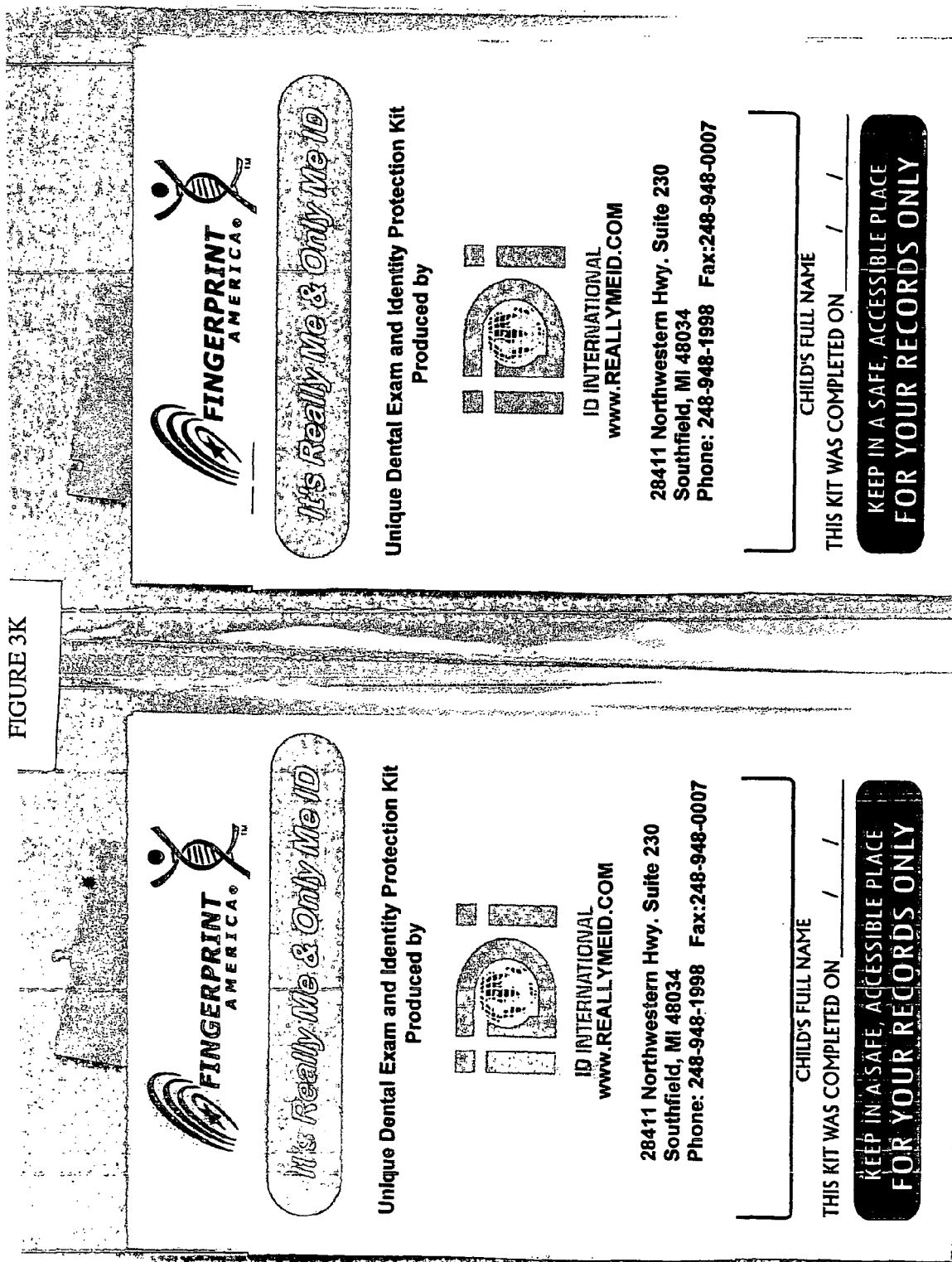
Figure 3L:
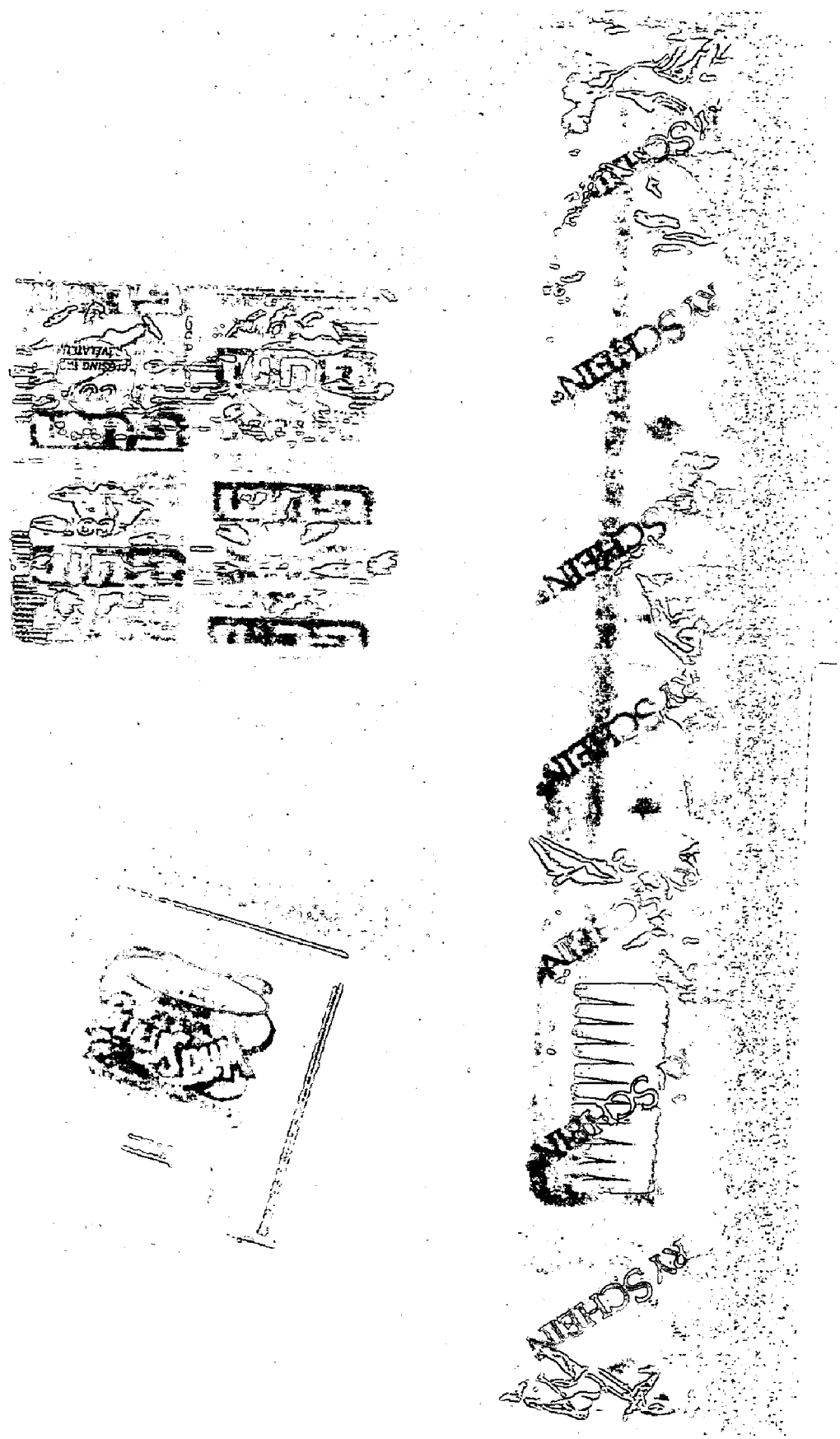
Figure 3M:

FIGS. 3A-3M illustrate the contents of an example kit. The figures show:

A) kit instructions, suggesting bringing various documents for recording;
B) a script, as shown in FIG. 2;
C) a form for recording insurance information;
D) a consent form, showing consent for subject imaging (photography or video recording);
E) data storage media, in this example recordable DVDs;
F) sealable containers (bags), for hair samples and the like;
G) a toothprint recording kit;
H) a blood-typing kit;
I) a mailing label, attached to a mailing envelope;
J) cheek spreaders;
K) forms on which dental records and other data can be recorded;
L) toothbrush, plaque disclosing tablets, and floss; and
M) a bracelet, identifying the wearer (the subject) as participating in an identification program.

The kit can be provided in a container, such as a box, having divisions sized to accept individual kit components.

Example Information Collection

A health professional, in this example, a dentist, is in possession of a high-definition video camera, DVD recorder (or flash drive), mouth mirrors (photo and oral), cheek retractors, blank DVDs, a script, a toothprint impression wafer, a fingerprint kit, a small plastic bag for a hair sample, x-ray equipment for dental x-rays, and a blood pressure monitor. Non-reusable items may be part of a kit sold by the health professional, or otherwise supplied by a subject or caregiver.

Audio-video information is obtained and stored on a DVD, including one or more of the following: voice recognition data, photographs of the body and mouth displaying identifying factors, fingerprints, dental x-rays, teeth impressions representative of subject dentition, and DNA samples, e.g. from the teeth impressions, saliva, or hair samples.

The DVD and all other material can be HIPAA compliant, so that all material is secure and only used with authorization. The DVD-R is recorded on a read-only disc and cannot be altered. The recorded DVD disk is given to the patient to take home for storage in a safe place. Relevant forms such as immunization forms, birth certificates, medical and dental insurance cards, other insurance documents, visas, passports, driver's license, and/or state ID card may also be recorded. A hand writing sample of a person completing the form can also be collected.

Preferably, a set of some or all of the identifier information is provided to the subject or the subject's representative, and a duplicate set, or more or less complete set, is stored by a storage provider, which may be the health professional.

Subject Identifier

A subject participating in the ID system may wear or otherwise carry an identifier, such as in the form of a bracelet, badge, clip, button, jewelry, ribbon, other adornment, RFID tag, clothing item, hat, ankle tag, electronic tether, other portable electronic device such as a cell-phone, implanted device, tattoo, modified footwear, or other form of identifier. The identifier may have a characteristic color scheme associated with a particular program, may provide a name, phone number, or electronic address e.g. of the subject, caregiver, medical professional, supplier or administrating business, and may include an authorization code allowing access to identifying information, or other information.

The identifier alerts a third party trying to identify the subject that the subject is participating in an identification program, and provides contact information for the subject's caregiver, other party such as a business supplying the kit or storing the identifying information, police, or other interested party.

The identifier need not contain any identification information, and may act only to alert a third party trying to identify the subject that there is identifying information available for the subject. In other examples, the identifier can contain identifying information for the subject. For example, a name can be supplied, the name being verified using the methods described herein. The identifier may also contain a data storage medium, on which some or all of the identifying information can be stored.

A reader can be supplied, allowing identifying data stored within the identifier to be read remotely. The identifier may also comprise a global positioning system, radio transmitter, transponder, or other communications system. The identifier can be part of an improved kit, or be supplied after identifying information has been collected. The subject can also be provided with a GPS locator phone.

Other Applications

Examples of the present invention provide a convenient way to organize and transport medical and dental information. Simple to use media (such as a DVD) can be viewed at home to review treatment plans, photos of any bodily condition or status, prescriptions, child growth chart, and can provide quick access reference in an emergency. Recorded data can be used to documents an individual's oral health status through life as changes occur.

Recorded identifying information provides documentation of basic medical and dental information, a unique tool for positive identification and authentication, a tool for documenting makeover changes of oral and bodily nature, and provides objective records of a subject's current and previous appearance or other condition. Placing medical-dental information in a subject's hands allows more effective communication and enhances their responsibility for self involvement of their care.

Recorded data can be used to document dental treatment rendered and status of maintenance. Subject compliance with medical or dental recommendations can be monitored and viewed at home or in a personal setting. Family history, such as a visual growth chart for children and maturing adults, can be preserved.

Other applications include use in security agencies (such as verification of identity of guard or suspected intruder), temporary staffing agencies, daycare centers, homeland security, custom agents and agencies, investment/banking institutions, insurance industry, identity/fraud protection agencies, house arrest supervision, and the like. Updates can be recommended every 3 to 5 years, thus corresponding to a full mouth x-ray series cycle for a patient or other subject.

Applications also include providing a visual tool to communicate with a medical professional, such as a dentist, for treatment or second opinions, serving as a method of identification and authentication, and assisting in determining the location of children and family members.

A GPS phone, or other GPS device, can be given to the subject, which can also be used to store identifying data or act as a subject identifier. Printed forms may show "VOID" on copies, or include other authentication. Subjects may be assigned an identity code, which can then be used in connection with corresponding identifying data. Subject identification can be made using the identity code, preserving privacy. Examples of the present invention can also be used to prevent identity theft, and in financial transactions.

The subject may also be a pet (such as a dog or cat), other mammal (such as a horse, cattle, or other livestock), other animal, or other living being. Examples of the present invention can be used to verify the identity of non-human animals, such as prize cattle, pedigree dogs, horses, and the like. Features such as unique markings or the retina can be imaged, and prints collected from the animal's nose, paw, ear, or other anatomical feature. A veterinary professional can collect animal identifying data, perform x-rays, image animals and associated documents, and the like.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

Patents, patent applications, or publications mentioned in this specification are incorporated herein by reference to the same extent as if each individual document was specifically and individually indicated to be incorporated by reference.

Having described my invention, I claim:

1. A kit for collection and storage of identification information specific to a subject and creation of a portable biometric electronic medical record for the same subject, the kit comprising:
   a dental impression element for collecting a dental impression of the teeth of the subject;
   a biological sample kit for collecting a biological sample, the biological sample selected from a group of biological samples consisting of a hair sample, a cheek cell sample, a blood sample, and a saliva sample;
   a fingerprint kit;
   a dental examination portion form for a health professional to perform a dental examination; and
   a portable data storage medium;
   wherein the kit for collection and storage is usable by a health care professional to perform the steps of:
   collecting a biological sample from the subject using the biological sample kit;
   obtaining a fingerprint of the subject using the fingerprint kit; and
   obtaining a dental characteristic of the subject. the dental characteristic selected from a group of dental characteristics consisting of a tooth imprint collected using the dental impression element, a dental chart, a dental image. and a dental x-ray; and
   recording a voice sample from the subject;
   the kit for collection and storage further being usable for collecting additional identification information specific to the subject, the additional identification information selected from a group of identification information consisting of information on name, age, height, weight, appearance, family, occupation, address, emergency contact, insurance, identifying features, and numbers from identifying documents; and
   storing information on the portable data storage medium, the stored information including at least the additional identification information and the voice sample.

2. A kit in accordance with claim 1, wherein:
   the kit further comprises an image recorder for recording a plurality of images.

3. A kit in accordance with claim 1, further comprising:
   an additional portable data storage medium for storing the same stored information on the additional portable data storage medium.

4. A kit in accordance with claim 1, wherein:
   the portable data storage medium is a memory device or a CD or DVD disc.

5. A kit for collection and storage of identification information specific to a subject and creation of a portable biometric electronic medical record for the same subject. the kit comprising:
   a dental impression element;
   a biological sample kit for collecting a biological sample, the biological sample selected from a group of biological samples consisting of a hair sample, a cheek cell sample, a blood sample, and a saliva sample;
   a fingerprint kit;
   a dental examination portion form for a health professional to perform a dental examination;
   a portable data storage medium:
   a cheek retractor/spreader to use with oral photographic mirrors;

a bubble envelope for return of a DVD for database;

a Consent Form for a dental examination and photographs and to identify person able to give consent other than subject if necessary;

a plaque disclosing tablet to assist in identification of the periodontal health status of the subject;

a toothbrush to identify brushing technique and instructions; and a sample of dental floss to identify and assist correct technique for usage wherein the kit for collection and storage is usable by a health care professional to perform the steps of:

collecting a biological sample from the subject using the biological sample kit;

obtaining a fingerprint of the subject using the fingerprint kit; and obtaining a dental characteristic of the subject;

the kit for collection and storage further being usable for collecting additional identification information specific to the subject, the additional identification information selected from a group of identification information consisting of information on name, age, height, weight, appearance, family, occupation, address, emergency contact, insurance, identifying features, and numbers from identifying documents; and storing information on the portable data storage medium, the stored information including at least the additional identification information.

6. A method for collection and storage of identification information specific to a subject and creation of a portable biometric electronic medical record for the same subject, the method comprising:

providing a kit for collecting identifying information and medical record information for a subject, the kit comprising:

a dental impression element;

a biological sample kit for collecting a biological sample, the biological sample selected from a group of biological samples consisting of a hair sample, a cheek cell sample, a blood sample, and a saliva sample;

a fingerprint kit; and a portable data storage medium;

a health care professional performing the steps of:

collecting a biological sample from the subject using the biological sample kit;

obtaining a fingerprint of the subject using the fingerprint kit;

obtaining a dental characteristic of the subject, the dental characteristic selected from a group of dental characteristics consisting of a tooth imprint collected using the dental impression element, a dental chart, a dental image, and a dental x-ray; and recording a plurality of subject images using an image recorder, the plurality of subject images of the subject selected from a group of subject images consisting of a dental intra and extra oral image, a facial image, a hand image, a retinal image, and body image;

recording a voice sample from the subject; and collecting medical record information;

collecting additional identification information specific to the subject, the additional identification information selected from a group of identification information consisting of information on name, age, height, weight, appearance, family, occupation, address, emergency contact, insurance, identifying features, and numbers from identifying documents;

storing information on the portable data storage medium, the stored information including at least the additional identification information, the plurality of subject images, the voice sample, and the medical record information; and providing the portable data storage medium to the subject.

7. A method in accordance with claim 6, wherein:

the plurality of images includes video images with audio, the recording a voice sample step comprising recording a voice sample as part of the video images.

8. A method in accordance with claim 6, wherein:

the health care professional is a dentist, a dental assistant, a physician or a physician assistant trained to perform this task.

9. A method in accordance with claim 6, further comprising the step of storing at least part of the stored information on in a location separate from the portable data storage medium.

10. A method in accordance with claim 9, wherein:

the location separate from the portable data storage medium is in a database.

11. A method in accordance with claim 9, wherein:

the location separate from the portable data storage medium is a location of the heath care professional.

12. A method in accordance with claim 6, wherein:

the kit further comprises an image recorder for recording the plurality of images.

13. A method in accordance with claim 6, further comprising:

providing an additional portable data storage medium and storing the same stored information on the additional portable data storage medium.

14. A method in accordance with claim 6, wherein:

the portable data storage medium is a memory device or a CD or DVD disc.

15. A method in accordance with claim 6, wherein the kit further comprises:

a cheek retractor/spreader to use with oral photographic mirrors;

a bubble envelope for return of a DVD for database;

a Consent Form for a dental examination and photographs and to identify person able to give consent other than subject if necessary;

a dental examination portion form for a health professional to perform a dental examination;

a plaque disclosing tablet to assist in identification of the periodontal health status of the subject;

a toothbrush to identify brushing technique and instructions; and a sample of dental floss to identify and assist correct technique for usage.

* * * * *

UNITED STATES PATENT AND TRADEMARK OFFICE
CERTIFICATE OF CORRECTION

| | | |
|---|---|---|
| PATENT NO. | : 7,916,900 B2 | Page 1 of 1 |
| APPLICATION NO. | : 11/365369 | |
| DATED | : March 29, 2011 | |
| INVENTOR(S) | : Joan E. Lanier | |

It is certified that error appears in the above-identified patent and that said Letters Patent is hereby corrected as shown below:

Column 8, line 26: subject. should read --subject,--

Column 8, line 30: image. should read --image,--

Column 8, line 55: subject should read --subject,--

Signed and Sealed this
Sixth Day of March, 2012

David J. Kappos
*Director of the United States Patent and Trademark Office*